(12) United States Patent  (10) Patent No.: US 8,132,769 B2
Metelski  (45) Date of Patent: Mar. 13, 2012

(54) STAND FOR A SURGICAL MICROSCOPE

(75) Inventor: Andrzej Metelski, Romanshorn (CH)

(73) Assignee: Leica Instruments (Singapore)Pte. Ltd., Singapore (SG)

( * ) Notice: Subject to any disclaimer, the term of this patent is extended or adjusted under 35 U.S.C. 154(b) by 375 days.

(21) Appl. No.: 12/371,492

(22) Filed: Feb. 13, 2009

(65) Prior Publication Data

US 2009/0218456 A1    Sep. 3, 2009

(30) Foreign Application Priority Data

Feb. 28, 2008 (DE) .................. 10 2008 011 639

(51) Int. Cl.
A47F 5/00 (2006.01)

(52) U.S. Cl. ......... 248/281.11; 248/280.11; 248/123.11; 359/365; 359/381

(58) Field of Classification Search ............ 248/280.11, 248/281.11, 123.11, 123.2, 125.7, 162.1; 359/382, 384, 368, 381, 419
See application file for complete search history.

(56) References Cited

U.S. PATENT DOCUMENTS

| | | | | |
|---|---|---|---|---|
| 4,166,602 A * | 9/1979 | Nilsen et al. | ............. | 248/280.11 |
| 4,881,709 A * | 11/1989 | Nakamura | ............... | 248/281.11 |
| 6,579,016 B2 * | 6/2003 | Chapman | ...................... | 396/428 |
| 6,592,086 B1 * | 7/2003 | Sander | ..................... | 248/123.11 |
| 7,472,872 B2 * | 1/2009 | Nakamura | ................. | 248/123.2 |
| 2005/0247831 A1 * | 11/2005 | Nakamura | ................. | 248/123.2 |

FOREIGN PATENT DOCUMENTS

| | | |
|---|---|---|
| DE | 9219240 | 10/2001 |
| DE | 101 33 018 | 1/2003 |
| DE | 10300620 | 11/2003 |
| EP | 0476551 | 3/1992 |
| EP | 0628290 | 12/1994 |
| EP | 0971451 | 5/1999 |

OTHER PUBLICATIONS

Related U. S. Appl. No. 12/371,518, filed Feb. 13, 2009 and assigned to Leica Microsystems (Schweiz) AG.
Related U. S. Appl. No. 12/371,440, filed Feb. 13, 2009 and assigned to Leica Microsystems (Schweiz) AG.
Related U. S. Appl. No. 12/390,116, filed Feb. 20, 2009 and assigned to Leica Microsystems (Schweiz) AG.

* cited by examiner

*Primary Examiner* — A. Joseph Wujciak, III
(74) *Attorney, Agent, or Firm* — Schlee IP International, P.C.; Alexander R. Schlee

(57) ABSTRACT

A stand for a surgical microscope is suggested, comprising a vertical support, at least one horizontal support, a first vertical articulation unit that is connected the horizontal support, a second articulation unit determining an oblique pivot axis, a displacement unit that is attached to the second articulation unit and has multiple degrees of freedom for displacement and balancing of an optics carrier carrying the surgical microscope, at least one pivot support encompassed by the displacement unit, and a displacer for displacing the optics carrier in an X direction extending horizontally and transversely to the oblique pivot axis. The pivot support comprises a pivotable parallelogram support and a holding arm that is attached to the pivotable parallelogram support and is configured such that it simultaneously serves as a displacer for displacing the optics carrier in the X direction.

17 Claims, 4 Drawing Sheets

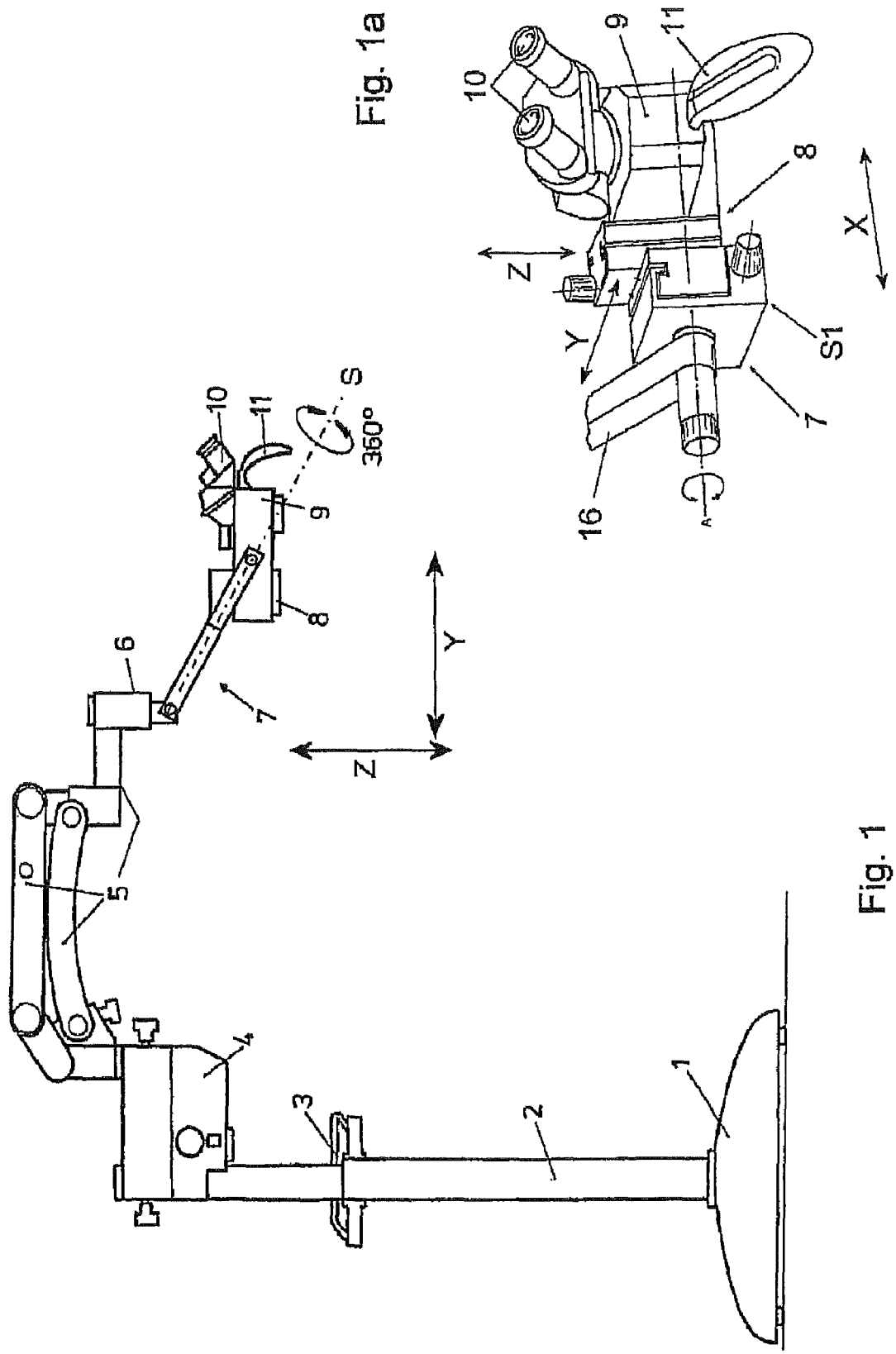

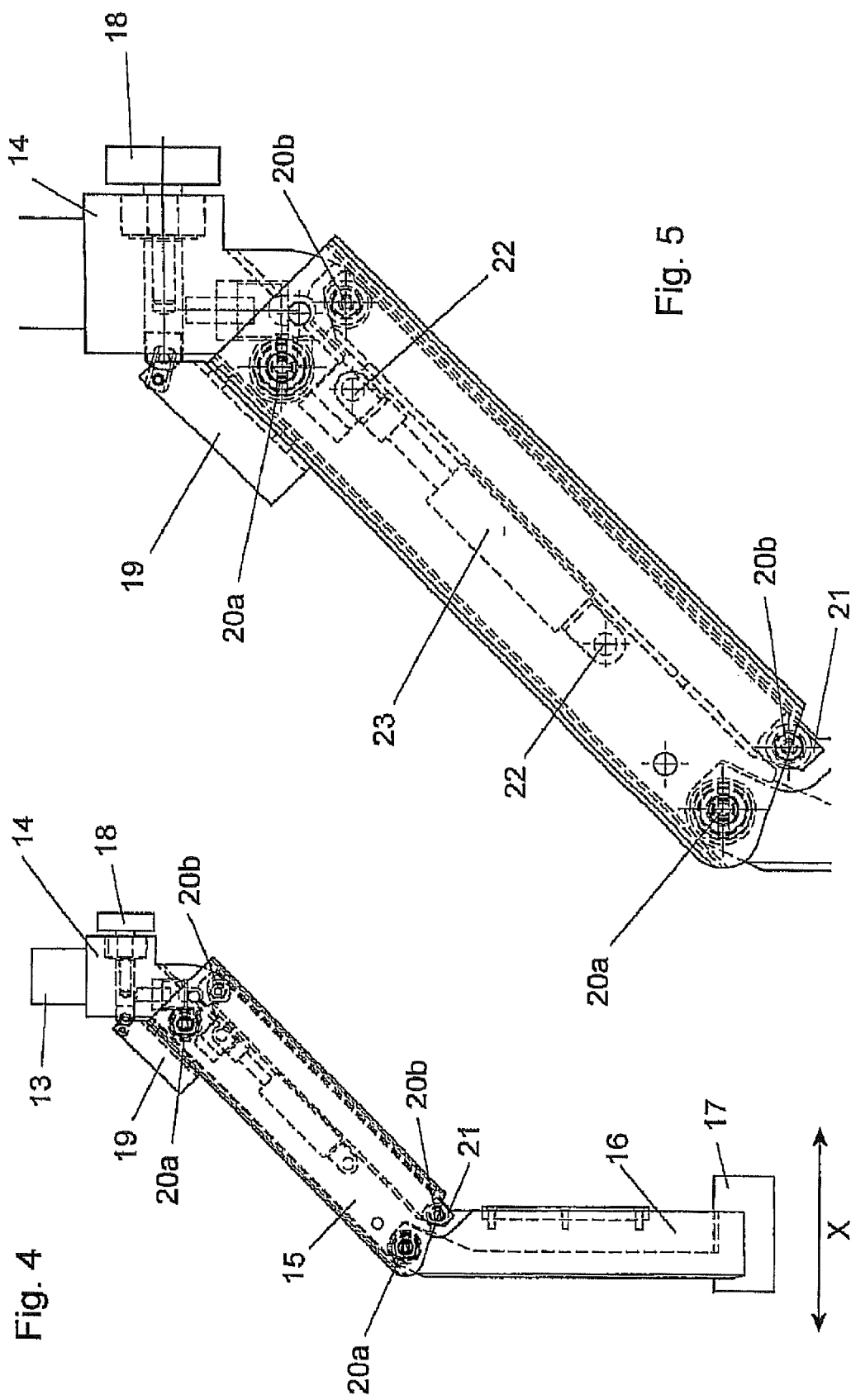

STAND FOR A SURGICAL MICROSCOPE

CROSS-REFERENCE TO RELATED APPLICATION

This application claims the priority of the German patent application DE 102008011639.4 having a filing date of Feb. 28, 2008, the entire content of which is herewith incorporated by reference.

BACKGROUND OF THE INVENTION

The invention relates to a stand, in particular for a surgical microscope.

A "stand" for purposes of the invention is a floor or wall stand or a ceiling mount.

Surgeons are increasingly making use of surgical microscopes that, because of their heavy weight, must be supported by stands. A number of reputable manufacturers, in addition to the Applicant, have brought to market stands that competently meet the load-bearing requirements of a surgical microscope in mechanical and static terms.

As is known, for example, from DE 101 33 018 A1, many conventional stands—e.g. those for surgical microscopes for ophthalmology—carry at their free end, between the microscope and the vertical stand support, an X and/or Y shifting unit for the microscope. This shifting unit serves for positioning the microscope, within millimeters, in the X and/or Y direction (in the plane parallel to the floor). An arrangement of this kind of the X-Y shifting unit (only the X shifting unit in the case of DE 101 33 018 A1 (FIG. 2)) is usually obtrusive for an operator, since the shifting unit means that a relatively large mass and a large volume must be moved, specifically not only the surgical microscope but also the entire suspension system, pivot support, etc. It is furthermore difficult, with this, to meet the necessary sterility requirements. The X displacement area must in some circumstances be operated by the surgeon, i.e. he or she must access it. This area remote from the surgical field must therefore also be kept completely sterile, which requires a drape. The latter is, however, in turn an impediment to vision and to the operation of controls. The X(-Y) displacement unit furthermore, because of its solid construction, considerably increases the weight on the horizontal extension arm, and as a rule must be compensated for by a corresponding compensation weight or braced by a correspondingly large stand foot. The entire carrier arm structure of the stand support, and if applicable also the entire stand base structure, must consequently have greater dimensions or must be dimensioned with a greater area. This all works against easy operability.

ENT surgical microscope (microscopes for ear, nose and throat surgery) must be easy to move because a relatively large number of adjustments must be made. In addition, such surgical microscope need to be fairly economical, since fewer resources are available for ENT surgical operations than in, for example, the neurological sector.

DE 92 19 240 U1 describes a displaceable stand for an optical observation device, having a flange for mounting the displaceable stand onto a stand base, onto a further stand, or onto the ceiling or a wall. The stand possesses a tilt joint about a horizontal tilt axis and a pivot joint about a pivot axis, by way of which the observation device is received rotatably and/or pivotably on the flange. The pivot joint is connected to the tilt joint with a rigid support extending obliquely downward. The observation device consequently cannot be displaced in a direction perpendicular to the drawing plane, which greatly limits the positional changes necessary during operation, and therefore the manageability of the observation device.

A "pivot support" is understood as that component or component group which is installed indirectly or directly on the horizontally extending support arm of the stand and receives, via an (in principle, horizontal) horizontal axis (A axis), the optics carrier in which the surgical microscope is held. The optics carrier and thus the surgical microscope are thus pivotable about this horizontal axis (A axis) and are thus intended to be tiltable with reference to that horizontal axis and balanceable preferably in two planes, so that with the brakes released, a surgeon can pivot the optics carrier and thus the surgical microscope about the horizontal axis in as resistance- and torque-free a manner as possible.

The horizontal axis is usually embodied at the lower part of the pivot support and equipped with a braking device or locking device that prevents any unintentional pivoting movement of the optics carrier and thus of the surgical microscope with reference to the pivot support.

The problem set forth in conjunction with DE 92 19 240 U1 is remedied in part by the technical approach described in DE 101 33 018 A1, which presents a stand, in particular for surgical microscopes, that is equipped with a stand base, a vertical support, one or more horizontal supports, a pivot support, and an X-Y-Z displacement unit (FIG. 3) for balancing on the pivot support. Displaceable X, Y, and Z displacement units are provided therein which position the optics carrier, and the microscope body installed thereon, in three dimensions.

In another variant of DE 101 33 018 A1 (FIG. 2), the horizontal displacement unit on which the pivot support can be displaced in a horizontal X direction is arranged not at the free end of the pivot support but on the upper part of the pivot support. This displaceability serves for balancing about an (if applicable) oblique vertical axis (cf. the rigid oblique support of DE 92 19 240 U1) about which the pivot support, and thus the horizontal axis and thus the optics carrier and the microscope, are pivotable. This pivoting movement, too, can be blocked by means of a brake or a locking device. The surgical microscope is thus pivotable in two spatial directions about the axes with the brakes or locking devices released, and can be balanced across the respective pivot axes.

A non-negligible disadvantage of the approach set forth results, however, from the physical dimension of the horizontal displacement unit for X shifting. Shifting of the pivot support in one direction is easily enabled, but this construction blocks or impedes a clear view by the surgical personnel of, for example, important observation areas, or impedes eye contact between surgeons and assistants. The relatively hefty unit also increases the moving mass of the stand, which must be accounted for in the strength calculations for all relevant components.

In the context of so-called "draping," i.e. covering the entire stand with a sterile cloth, it is also disadvantageous when larger mechanical external accessories are present in the region of the adjusting devices, since the drape can then become even more visually obtrusive.

To ensure better vision for the operator, DE 103 00 620 A1 proposes interconnecting the articulation units at the end of the horizontal support arm with the microscope holder unit via a laterally curved support. Because of its C-shaped appearance, such a support is also called a "C support." With this approach, an X-Y displacement unit is indeed moved closer to the vertical stand support so that the X-Y positioning unit moves not only the microscope but additionally also part of the horizontal stand support, but this construction also does not yield easy and precise adjustment of the microscope along the aforesaid X direction. Inertia has a very obtrusive effect in this context. This construction therefore also does not possess a complete balancing apparatus for the surgical microscope.

EP 0628290 presents a very complex stand apparatus for an item of medical/optical equipment. It encompasses a pair of vertical parallel links and a pair of horizontal parallel links, which are combined with one another to form a parallelogram support. An intermediate portion of one of the vertical links is connected pivotably, at a pivot point, to a stand that is arranged on a surface. A counterweight is provided in order to equalize the weight. The parallelogram support is thus equipped so as to hold the medical/optical equipment item in stationary fashion in a floating state. One of the horizontal links of the parallelogram support is elongated in order to form a support link, and a substantially vertical front link is mounted pivotably on the support link at a front end thereof, the medical/optical equipment item being held at the lower end of the front link. The approach that is proposed contributes to easy and precise displacement of the microscope in a vertical direction, but a similar displacement capability in the horizontal direction, i.e. along the X direction, is still not provided.

EP 0917451 B1 describes a pivot support for a surgical microscope on a stand having vertical and horizontal supports with a suspension system. A prerequisite for the approach indicated therein was principally to dispense with parallelogram supports and avoid their disadvantages, and nevertheless to enable torsion-free mounting of a surgical microscope. For that purpose, the parallelogram support was replaced by a combination of two two-armed angled levers, which are rotatably interconnected and which additionally receive at both ends identical lever gearing systems which transfer the moments so that (in a manner comparable to a parallelogram support) the center of gravity of the load can be held in space. The two-armed angled lever is, however, constructed with great complexity from many precise components, and has dimensions approximately comparable to those of the aforementioned X (horizontal) displacement unit of DE 101 33 018 A1.

SUMMARY OF THE INVENTION

A first goal of the invention is therefore to create a stand, in particular for surgical microscopes, that one the one hand enables unimpeded movement of the microscope in space, and on the other hand does not impede a clear view by operating personnel of the area to be observed.

Proceeding from the aforementioned existing art, it is thus a first object of the invention to modify the support structure of the stand in such a way that the support units used ensure an appropriate and balanceable displacement of the optics carrier along an X direction, but at the same time, because of their relatively small, slender dimensions, do not represent barriers to a view of, for example, co-workers or patients.

The inventor has recognized that the horizontal displacement unit, arranged in the upper region, of DE 101 33 018 A1 can be replaced by a lateral pivoting movement of the pivot support. The use of a parallelogram support instead of the previously only one-part pivot support ensures, according to the present invention, that the respective horizontal position of axis A (cf. FIG. 2 of DE 101 33 018 A1), and thus the vertical position of the microscope holder or optics holder and of the microscope, remains unchanged and does not tilt away to the side.

This first object is thus achieved by a pivot support that comprises a displaceable (pivotable) parallelogram support and a holding arm, mounted thereon, that is equipped so that it simultaneously serves as a means for displacing the optics carrier along the X direction.

The MC1 of the existing art also exhibited a further problem, however:

In order, however, to enable sufficient balancing for the surgeon even, and especially, in those configurations of the system in which, for example, assistant's tubes or lateral add-on units are to be attached to the optics carrier, a consequence of the known arrangement according to the MC1 is that these add-on units can collide, during the balancing procedure, with the slide that is responsible for vertical displacement. The freedom of movement of the microscope was therefore limited in the case of the known unit. On the other hand, homogeneity of the movements was thereby also reduced.

In accordance with the existing art in the context of the MC1, in order to reduce this problem the procedure of balancing out was made easier by attaching an add-on weight. The add-on weight, with its mass of approximately 3.5 kg, was attached on the side of the optics carrier located opposite the add-on units on the microscope. The add-on units were thus balanced out across the A axis at least in terms of the Y direction (with the microscope in the normal position).

The disadvantage of this known weight compensation is that it considerably increases the total weight, which results in increased inertia when pivoting. Installation or removal of this add-on weight also required additional effort. This method is therefore time-consuming, and moreover results in increased forces and moments on the stand as a whole because of the greater total weight (see also e.g. EP-0476551 A1). The add-on weight produces not only an increase in torque (moment of resistance to rotation) during the displacement procedure, but also greater friction in every bearing of the entire stand, thus increasing the overall inertia of the stand and limiting its mobility. Homogeneity of the movements of the stand is also thereby reduced. In addition, the dimensions of the carrier arms of the stand (and of all other load-bearing components) of course also had to be correspondingly enlarged, which in turn considerably increased the total weight of these components and thus also the cost of the stand.

In present-day surgical practice, however, surgical microscopes not only need to meet standard requirements in terms of optical quality, bright illumination, compact design, and maximum flexibility, but also must incorporate additional operational aspects. Consideration must now be given, for example, to the fact that the number of surgical operations per day has risen. The time needed to set up a surgical microscope for the next operation is becoming increasingly important. As an essential component of the operating-room infrastructure, the surgical microscope has a significant influence on costly preparation time.

The second object underlying the invention is therefore that of even further improving an apparatus that has been improved in accordance with the first object, which apparatus enables relatively faster and simpler, and complete, balancing of the surgical microscope without an add-on weight. This is intended to significantly reduce or eliminate the aforementioned disadvantages of the existing art. The intention is therefore for all possible configurations of the surgical microscope to be as easy as possible for the surgeon to balance out across the A axis.

The inventor has further recognized that in order to achieve the second stated object, weight must be reduced at least in the region of the optics carrier, without limiting movements for a precise balancing procedure. In particular, the intention was to remove the additional compensation weight. If this were successful, then in combination with the aforesaid manner of achieving the first object, an ideal design for the surgical microscope would be found. This second object is not achieved or suggested by any of the known balancing device, especially because this object had not hitherto been stated in any of the known documents (including DE 10133018 A1) of the existing art. In addition to replacement of the add-on weight, a further intention is therefore to prioritize weight saving, cost reduction, and smooth operation of the stand.

This second object is achieved, according to the present invention, by an aforementioned stand, further comprising a balancing apparatus for a surgical microscope for balancing an optics carrier held by the pivot support, said optics carrier being rotatable around a first rotational axis in relation to the pivot support; said balancing compensating for the use with and without a microscope holder holding the surgical microscope and with and without add-on units, the balancing apparatus comprising: a Y displacement unit comprising a first slide for displacement of the optics carrier in a Y direction; and a Z displacement unit comprising a second slide for displacement of the optics carrier in a Z direction, wherein the first slide provides for displacement of the optics carrier in a direction transversely to the first rotational axis and transversely to the displacement by the second slide in the Z direction; and the first slide is connected between the pivot support and the second slide and to said second slide such that the weight of the second slide acts as a compensation weight for compensating the weight of the optics carrier with and without the microscope holder holding the surgical microscope and with and without the add-on units via the first rotational axis.

The invention in accordance with the first and the second object is further explained, symbolically and by way of example, with reference to the attached FIG. 6. It is to be understood that the measures for achieving the first object can be integrated into the embodiments according FIGS. 1 to 5 below, but are not absolutely necessary, since the novel X displacement system itself already provides a significant and inventive improvement with respect to existing balancing apparatuses.

Be it also noted expressly at this juncture that the overall construction of the stand can be even further improved by the fact that in addition to the two inventions indicated above, a third invention is also integrated. This is described in U.S. patent application Ser. No. 12/371,518 filed on Feb. 13, 2009. Reference is made with this present patent application to the aforementioned patent application. Reference is also made to a further U.S. patent application Ser. No. 12/371,440 filed on Feb. 13, 2009. All the inventions in accordance with these three patent applications can advantageously be integrated for optimum configuration of a stand, for which reason the contents of the two aforementioned The Parts List, together with the content of the Claims, is a constituent of the disclosure.

The invention will be further explained, symbolically and by way of example, with reference to Figures. The Figures are described continuously and in overlapping fashion. Identical reference characters denote identical components; reference characters having different indices indicate similar or functionally identical components.

BRIEF DESCRIPTION OF THE DRAWINGS

In the drawings:

FIG. 1 shows the overall configuration of a surgical microscope having a stand base, vertical support, control unit, horizontal support, pivot support, and microscope unit;

FIG. 1a shows a configuration in accordance with the manner of achieving the second object (slide arrangement S1, S2);

FIG. 4 is a further depiction of the pivot support of FIG. 2;

FIG. 5 shows the parallelogram support of the pivot support of FIG. 4 at enlarged scale.

DETAILED DESCRIPTION OF THE DRAWINGS

Figure 3:
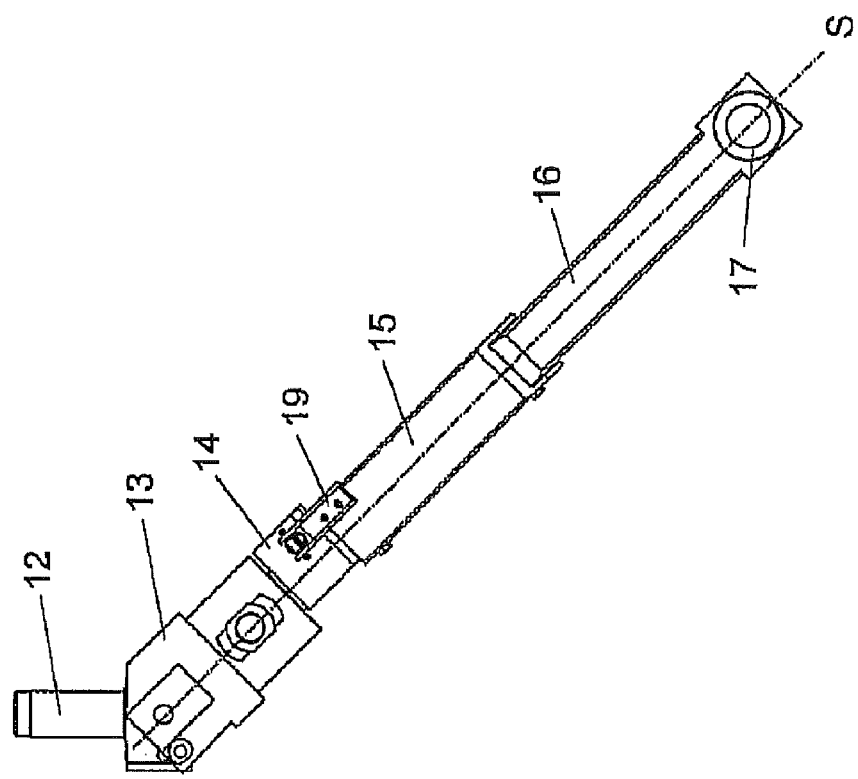
FIG. 3 is a side view of the pivot support of FIG. 2 from the same direction as in FIG. 1.

FIG. 1 depicts a schematic general configuration of a surgical microscope according to the present invention. A stand base 1 is visible herein, from which a vertical support 2 protrudes. For convenient movement of the caster-mounted stand, a grip 3 is attached to vertical support 2. Installed on vertical support 2 is a control unit 4 on which horizontal supports 5 are braced. In the embodiment depicted, the horizontal supports end in an articulation unit 6 that holds a pivot support 7, with optics carrier 9 mounted thereon, pivotably about a pivot axis S. Located at the other end of pivot support 7 is Y-Z displacement unit 8. The binocular tube having eyepieces 10, and an ergonomically shaped handle 11, are also depicted.

FIG. 1a shows, in the upper part, a configuration according to the manner of achieving the second object (slide arrangement S1, S2) that is preferably arranged at the lower end of pivot arm 7. Regarding further details of this configuration, the reader is referred to the Figures of U.S. patent application Ser. No. 12/371,440 filed on Feb. 13, 2009.

Figure 2:
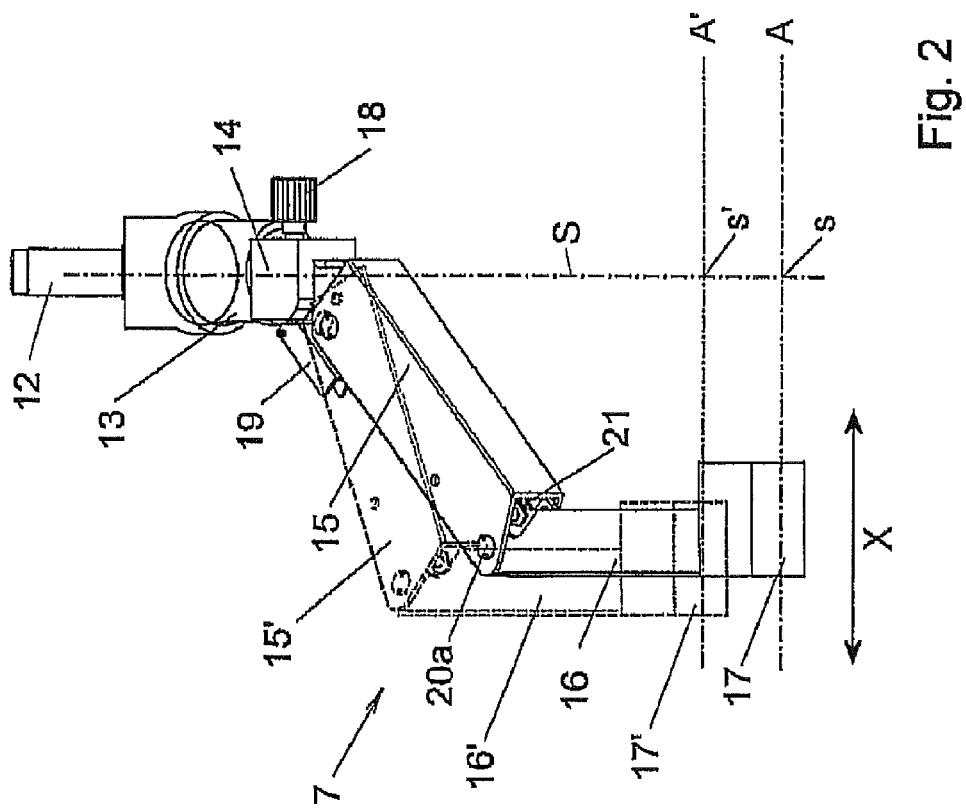
FIG. 2 is a perspective plan view of an embodiment of the pivot support according to the present invention of FIG. 1.

FIG. 2 depicts pivot support 7 in a perspective plan view. Pivot support 7 comprises at its upper end, adjacent to horizontal support 5, an axis pin 12 with which pivot support 7 is rotatably mounted and held in vertical articulation unit 6. Axis pin 12 adjoins a further articulation unit 13 that mounts pivot support 7 rotatably about the S axis (the actual pivot axis) drawn with a dot-dash line in FIG. 1. Attached to articulation unit 13 is a further displacement unit 14 that serves for positioning of a parallelogram support 15. Parallelogram support 15 is movably connected at its other end to a holding arm 16, and the latter carries at its other, lower end a further articulation unit 17 that rotatably mounts Y-Z displacement unit 8 (see FIG. 1). Displacement unit 14 comprises a displacement screw 18 that is connected, in a manner to be presented in more detail below, to a displacement element 19. In the exemplifying embodiment depicted, displacement element 19 is fixedly connected to parallelogram support 15. In the example depicted, holding arm 16 is connected via pivot pins 20a, b to movable parts 21 of parallelogram support 15 in the interior of the body of parallelogram support 15.

FIG. 3 is a side view of pivot support 7 from the same direction as in FIG. 1, i.e. from the left. As is evident, pivot support 7 extends obliquely downward, approximately parallel to the orientation of pivot axis S. Further articulation unit 17 contains a sleeve for reception of a corresponding pin of Y-Z displacement unit 8 (not depicted).

FIGS. 4 and 5 show a further depiction of pivot support 7 in which the internal components of parallelogram support 15 are drawn with dashed lines. Movable parts 21 of parallelogram support 15 are arranged inside the body (bent from sheet metal in the embodiment depicted) and, as is usual for parallelogram links or parallelogram supports, interconnected via pivot pins 20. In order to achieve easier operation for X-direction displacement by means of displacement screw 18, at least one energy reservoir 23, which is attached via mounting eyes 22 to the body and to movable part 21, is also located in the interior of the body. In contrast to conventional parallelogram supports having an energy reservoir, this energy reservoir does not have a bracing function in the energy-storage direction against the weight of the surgical microscope, but instead has exclusively the function of facilitating displacement of the displacement screw. The displacement screw accordingly is preferably self-locking.

Instead (or alternatively), or for assistance of the energy reservoir, an electric motor could also be provided in the context of a further development of the invention. In the alternative case, the electric motor can also take on the function of the displacement screw, in which case the electric motor (energy reservoir) also takes on a bracing function. It is preferred in this case if the electric motor is embodied in self-locking fashion, so that no unintentional displacement can occur in the zero-current state.

A variety of components known to one skilled in the art are usable as energy reservoir 23. A helical spring or a gas spring, for example, can be used. If a gas spring is used, less energy expenditure is necessary upon displacement of displacement screw 18. In a preferred exemplifying embodiment, displacement screw 18 is motor-driven. Energy reservoir 23 could then actually be omitted if movable parts 21 are installed with a tight fit relative to the body of parallelogram support 15, and if the position of parallelogram support 15, once established, is maintained by the friction that exists.

Figure 6:
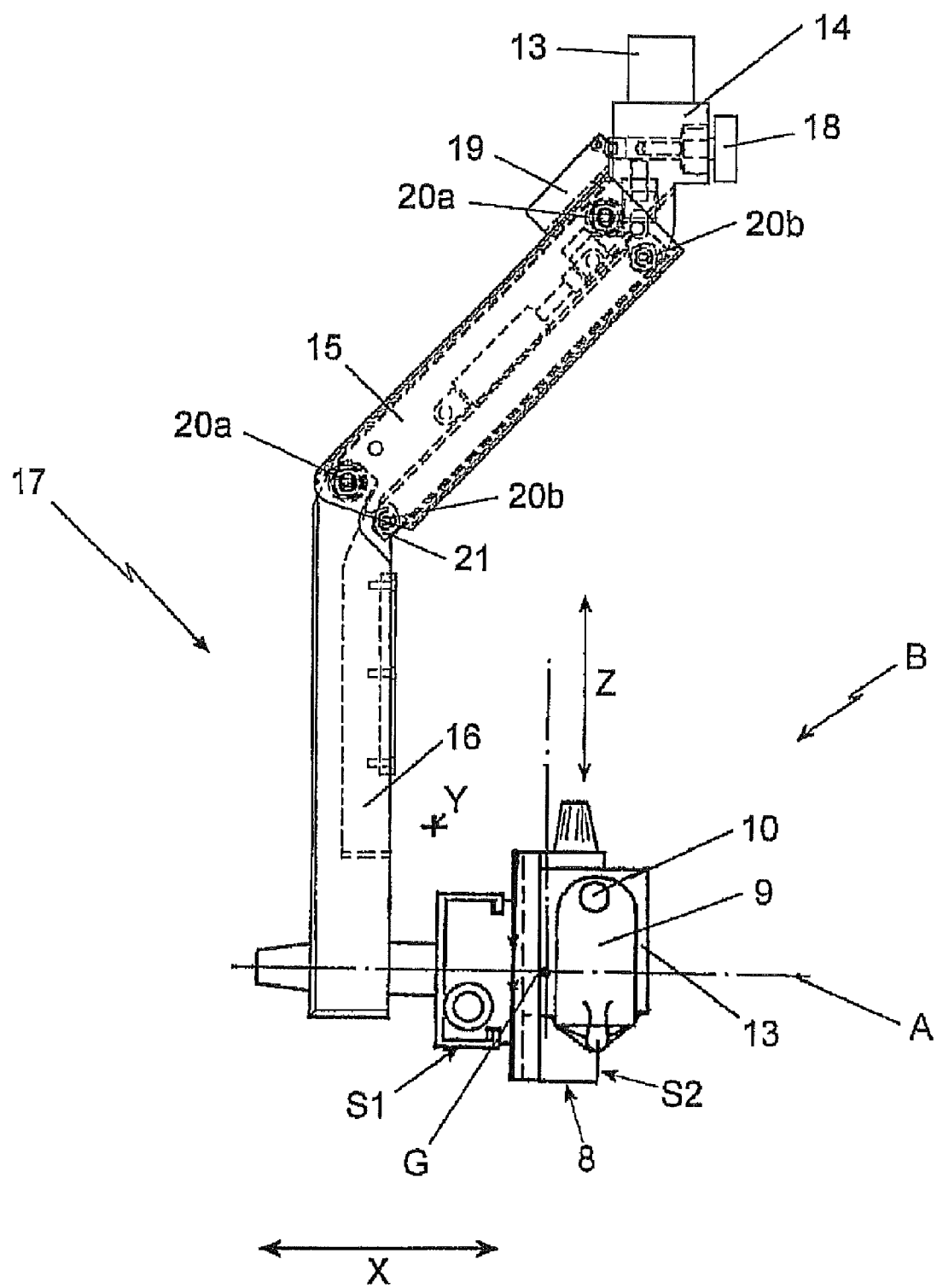
FIG. 6 shows the configuration according to the present invention in accordance with the manner of achieving the first object, with the addition of a novel slide arrangement according to the second object.

FIG. 6 shows the configuration according to the present invention according to the manner of achieving the first object, with the addition of a novel slide arrangement according to the second object (cf. FIG. 1a and Patent Application 10 2008 011 640, submitted on the same date). Thanks to this configuration, the surgical microscope becomes optimally balanceable in six degree of freedom.

When the surgical microscope is in service, movements of the surgical microscope can be performed in the three principal directions X, Y, and Z. The three principal directions X, Y, and Z are to be understood as follows: the X direction as approximately left-right in the plane of the drawing with respect to the observer, the Y direction as a direction front to back and perpendicular to the drawing plane, and the Z direction as an up and down direction approximately parallel to the X direction.

In the example depicted, the position of parallelogram support 15 and thus of pivot support 7 is determined, or modified or aligned, by way of displacement screw 18. Clockwise rotation of displacement screw 18 causes displacement element 19 to move away from displacement unit 14, with the result that parallelogram support 15, loaded by energy reservoir 23, pivots to the right in FIG. 2, i.e. along direction X, since although the orientation of holding arm 16 remains unchanged, its longitudinal axis is shifted parallel to itself.

Counterclockwise rotation of displacement screw 18 causes displacement element 19 to be pulled closer to displacement unit 14 by means of displacement screw 18. Parallelogram support 15, fixedly connected to displacement element 19, is thereby pivoted to the left in FIG. 2, i.e. once again along direction X, against the force of energy reservoir 23, and the orientation of holding arm 16 remains unchanged. By means of an appropriate embodiment of displacement screw 18, a coarse but also a fine adjustment or alignment of pivot support is accomplished. In the context of the invention these displacement screws can of course also be replaced by electric drive systems, and operated remotely.

With the new pivot support 7, instead of the previous linear transverse motion in the upper region of pivot support 7, a pivoting motion is carried out in the lower part of pivot support 7 and causes optics carrier 9 to pivot along an arc about an axis in the upper region of pivot support 7. But because the upper part of pivot support 7 is embodied, according to the present invention, as a parallelogram support, the pivot axis remains in the lower part of pivot support 7 in an unchanged, preferably horizontal, position.

The principal advantage of the proposed solution that can be mentioned is that the previously utilized complete horizontal displacement unit in the vicinity of the upper articulation units, in addition to the pivot support, is eliminated; and the displacement parts that enable this pivoting movement have only a minimal physical size and therefore do not represent an obstacle to vision or the like. According to a particular embodiment of the invention, the parallelogram support is constructed in nested fashion, so that only a portion of the link is visible. This contributes to a more robust construction and to a lower risk of contamination. The parallelogram support furthermore ensures corresponding rigidity in directions deviating from its plane, which makes the dimensioning of pivot support 7 easier and ultimately means that lower forces are acting on the stand. A parallelogram support system of this kind can moreover be completely (perfectly) balanced by firstly moving the center of gravity of the microscope onto axis A (Y-Z displacement), then bringing axis A into intersection with axis S and then shifting it transversely to axis S until the center of gravity of the microscope is also located on axis S. In this location the microscope is perfectly balanced in three axes and is therefore practically weightless for the operator.

The Parts List below is a constituent of the description. The constructions, apparatuses, and details indicated in the Claims are also deemed to be disclosed as if in the context of the description.

The reference characters in the aforementioned mutually referenced Applications of the same application date may differ slightly between the Applications. This does not mean, however, that the components bearing the different reference characters in the different applications are differently configured.

List of Component Parts

1 Stand base
2 Vertical support
3 Grip
4 Control unit
5 Horizontal support
6 Articulation unit
7 Pivot support
8 Y-Z displacement unit
9 Optics carrier
10 Eyepiece 11 Handle
12 Axis pin
13 Articulation unit
14 Displacement unit
15 Parallelogram support
16 Holding arm
17 Articulation unit
18 Displacement screw
19 Displacement element
20a, b Pivot pins of parallelogram support
21 Movable part
22 Mounting eye
23 Energy reservoir
S Pivot axis

The invention claimed is:

1. A stand for a surgical microscope, comprising:
a vertical support;
the vertical support further comprises at least one horizontal support having a first end facing toward the surgical microscope;
a first vertical articulation unit that is connected said first end;
a second articulation unit determining an oblique pivot axis and being connected to the first vertical articulation unit;
a displacement unit that is attached to the second articulation unit and has multiple degrees of freedom for displacement and balancing of an optics carrier carrying the surgical microscope;
at least one pivot support encompassed by the displacement unit; and
means for displacing the optics carrier in an X direction extending horizontally and transversely to the oblique pivot axis, said means for displacing being provided at the pivot support; wherein said pivot support comprises:
a pivotable parallelogram support having a first carrier arm and a second carrier arm, the second carrier arm extending in parallel to the first carrier arm; and
a holding arm that is attached to the pivotable parallelogram support and is configured such that it simultaneously serves as a means for displacing the optics carrier in the X direction; wherein
the pivot support is attached with a first end directly to the second articulation unit and with a second end directly to a Y-Z displacement unit for the optics carrier.

2. The stand according to claim 1, wherein the pivot support is provided with an additional displacement unit that determines the position of the parallelogram support with reference to the second articulation unit.

3. The stand according to claim 2, wherein the additional displacement unit contains a displacement screw that protrudes through the parallelogram support and is connected in an articulated fashion at one of its ends to a displacement element mounted to the parallelogram support.

4. The stand according to claim 2, wherein the additional displacement unit comprises an electric drive system.

5. The stand according to claim 3, wherein at least one of the movable parts of the parallelogram support and of the displacement screw are self-locking maintaining positions of the parallelogram support by a self-locking force.

6. The stand according to claim 1, wherein the parallelogram support is provided with an energy storing device assisting with a stored force in a displacement movement.

7. The stand according to claim 6, wherein the energy storing device is at least one of a spring and a gas damper that interconnects and supports movement of the movable parts in the interior of the parallelogram support.

8. The stand according to claim 6, wherein the energy storing device comprises an electric motor.

9. The stand according to claim 1, wherein the parallelogram support has a closed, integrated design having the first carrier arm arranged inside the second carrier arm.

10. The stand according to claim 1, wherein the displacement unit has six degrees of freedom.

11. The stand according to claim 1, further comprising a balancing apparatus for a surgical microscope for balancing an optics carrier held by the pivot support, said optics carrier being rotatable around a first rotational axis in relation to the pivot support; said balancing compensating for the use with and without a microscope holder holding the surgical microscope and with and without add-on units, the balancing apparatus comprising:
a Y displacement unit comprising a first slide for displacement of the optics carrier in a Y direction; and
a Z displacement unit comprising a second slide for displacement of the optics carrier in a Z direction, wherein
the first slide provides for displacement of the optics carrier in a direction transversely to the first rotational axis and transversely to the displacement by the second slide in the Z direction; and
the first slide is connected between the pivot support and the second slide and to said second slide such that the weight of the second slide acts as a compensation weight for compensating the weight of the optics carrier with and without the microscope holder holding the surgical microscope and with and without the add-on units via the first rotational axis.

12. The stand according to claim 11, wherein the optics carrier is connected to the slide of the Z displacement unit and movable via said slide.

13. The stand according to claim 11, wherein the first slide has a first guidance element and a first insert axially displaceable in the first guidance element, the first insert is secured to a second guidance element of the second slide, a second insert of the second slide is arranged axially displaceably in said second guidance element, and the second insert is connected to the optics carrier.

14. The stand according to claim 11, wherein the optics carrier along with the second slide is held by a holding part that carries in integrated fashion an electronic system and at least one sensor for motors for remote operation of the first and second slides.

15. The stand according to claim 13, wherein the second insert and the optics carrier are integrally formed.

16. The stand according to claim 11, wherein the first and the second slide are combined into a cross-slide and the first insert of the first slide is integrally formed with the second guidance element of the second slide.

17. The stand according to claim 11, wherein the drive systems for the first and second slides are electrified and drivable in sensor-controlled fashion by remote control.

* * * * *